(12) United States Patent
Kirino

(10) Patent No.: US 8,686,059 B2
(45) Date of Patent: Apr. 1, 2014

(54) BASE AND RADICAL GENERATOR, COMPOSITION USING SAME AND METHOD FOR CURING SAME

(75) Inventor: Manabu Kirino, Tokyo (JP)

(73) Assignee: Three Bond Co., Ltd., Tokyo (JP)

( * ) Notice: Subject to any disclaimer, the term of this patent is extended or adjusted under 35 U.S.C. 154(b) by 0 days.

(21) Appl. No.: 13/378,753

(22) PCT Filed: Jun. 16, 2010

(86) PCT No.: PCT/JP2010/060242
§ 371 (c)(1),
(2), (4) Date: Dec. 16, 2011

(87) PCT Pub. No.: WO2010/147161
PCT Pub. Date: Dec. 23, 2010

(65) Prior Publication Data
US 2012/0095124 A1  Apr. 19, 2012

(30) Foreign Application Priority Data

Jun. 17, 2009  (JP) .................. 2009-144660

(51) Int. Cl.
C08F 2/50 (2006.01)
C08B 37/00 (2006.01)
C08F 2/46 (2006.01)
B29C 71/04 (2006.01)
C08G 61/04 (2006.01)

(52) U.S. Cl.
USPC ............ 522/26; 522/7; 522/6; 522/71; 522/1; 520/1

(58) Field of Classification Search
USPC ................. 522/26, 7, 6, 71, 1; 520/1
See application file for complete search history.

(56) References Cited

U.S. PATENT DOCUMENTS 3,888,827 A * 6/1975 Matueda et al. ............ 528/113

FOREIGN PATENT DOCUMENTS

| EP | 0555749 A1 | 8/1993 |
| EP | 0599571 A2 | 6/1994 |
| JP | 49-127911 A | 12/1974 |
| JP | 50-76199 | 6/1975 |
| JP | 4330444 A | 11/1992 |
| JP | 05-134339 | * 5/1993 |
| JP | 2000-229927 A | 8/2000 |
| JP | 200326772 A | 1/2003 |
| JP | 2008-001857 | * 1/2008 |
| JP | 2009-120683 A | 6/2009 |
| WO | WO 02051905 A1 | 7/2002 |
| WO | 2008/001637 A1 | 1/2008 |
| WO | 2008/016057 A1 | 2/2008 |

OTHER PUBLICATIONS

Bradley. "Chemistry & Technology of UV & EB Formulation for Coatings, Inks & Paints." pp. 479-545, 1998.
Cameron et al. "Base Catalysis in Imaging Materials. 1. Design and Synthesis of Novel Light-Sensitive Urethanes as Photoprecursors of Amines." J. Org. Chem., vol. 55, pp. 5919-5922, 1990.
Frechet et al. "Photogenerated Amines and Diamines: Novel Curing Systems for Thin Film Coatings." Polym. Mat. Sci. Eng., vol. 64, pp. 55-56, 1991.
Frechet. "The photogeneration of acid and base within polymer coatings: Approaches to polymer curing and imaging." Pure & Appl. Chem., vol. 64, No. 9, pp. 1239-1248, 1992.
Mochizuki et al. "Novel Photosensitive Polyimide Precursor Based on Polyisoimide Using an Amine Photogenerator." Macromolecules, vol. 28, pp. 365-369, 1995.
International Search Report (PCT/ISA/210), dated Aug. 31, 2010, issued by the International Searching Authority in corresponding International Application No. PCT/JP2010/060242.
Written Opinion (PCT/ISA/237), dated Aug. 31, 2010, issued by the International Searching Authority in corresponding International Application No. PCT/JP2010/060242.
European Search Report, dated Oct. 12, 2012, issued in corresponding European Patent Application No. 10789535.1.
Office Action issued Jan. 10, 2014 from the Chinese Patent Office in Chinese Application No. 201080026621.7.

* cited by examiner

*Primary Examiner* — Ling Choi
*Assistant Examiner* — Jessica E Whiteley
(74) *Attorney, Agent, or Firm* — Sughrue Mion, PLLC

(57) ABSTRACT

The present invention relates to an aminimide compound having a structure represented by the following general formula (I) in the molecule thereof, relates to a curable composition using the aminimide compound and relates to a method for curing the composition;

[Chem. 1]

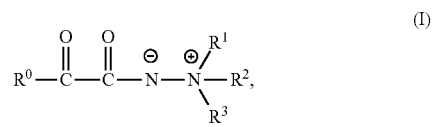

in which $R^0$ represents a hydrogen atom, an alkyl group which may have an optional substituent, an aryl group which may have an optional substituent, or a heterocyclic residue which may have an optional substituent. $R^1$, $R^2$ and $R^3$ each independently represent a hydrogen atom, or an optional substituent. However, at least two of $R^1$, $R^2$ and $R^3$ may bond to each other to form a cyclic structure.

10 Claims, 1 Drawing Sheet

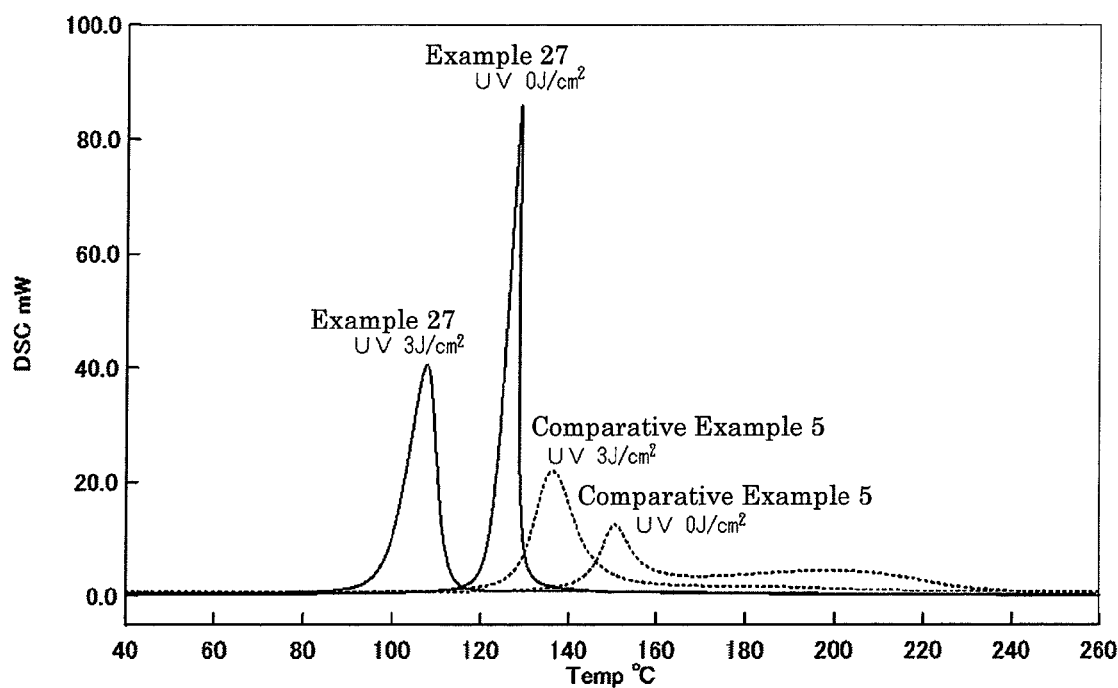

BASE AND RADICAL GENERATOR, COMPOSITION USING SAME AND METHOD FOR CURING SAME

TECHNICAL FIELD

The present invention relates to an aminimide compound that generates a base through heating at a lower temperature than before and/or through irradiation with active energy rays, and generates a radical species through irradiation with active energy rays. The present invention also relates to a curable composition using the aminimide compound and to a method for curing the composition.

BACKGROUND OF THE INVENTION

A curing technology with active energy rays enables low-temperature curing, process reduction, short-time curing and microfabrication as compared with existing thermal curing techniques, and is widely used for adhesives, sealants, coating agents, resists and the like, making full use of the characteristics thereof. The curing method mainly used in curing with active energy rays is broadly divided into radical polymerization and cationic polymerization. A composition to be cured through radical polymerization comprises, as the main ingredients thereof, a photoradical generator and a (meth)acrylate resin, and is characterized in that it is cured immediately after irradiation with active energy rays, but has some problems in that, in general, the adhesion power thereof is low, the curing shrinkage is large and the heat resistance is poor. A composition to be cured through cationic polymerization comprises a photocation generator such as a diaryliodonium salt, a triarylsulfonium salt or the like, and a cationic polymerizing resin such as an epoxy resin, an oxetane resin, a vinyl ether resin or the like, in which the photocation generator generates acid through irradiation with active energy rays to cure the cationic polymerizing resin therein. The cationic polymerization is characterized by rapid curability, high adhesion power and low curing shrinkage, but has some problems in that there may occur curing failure owing to the moisture or some slight basic contamination of the surface of the adherend, and the adherend of a metal or an inorganic material, if used, may be corroded by the strong acid existing in the system.

As one means for solving the problems with such cationic polymerization, anionic polymerization with a photobase generator capable of generating a base through irradiation with active energy rays has become studied recently. As the photobase generator, for example, generally known are carbamate derivatives and oxime ester derivatives; and these compounds generate primary or secondary amines through irradiation with active energy rays and are used in curing of epoxy resins (Non-Patent Documents 1 to 4). The technique of generating a base with active energy rays is much used in photoresist technology. For resists, curing mode of anionic polymerization which is little troubled by termination reaction is much used, for the purpose of securing the dimensional stability of the developed edges (Non-Patent Document 5, Patent Documents 1 to 3).

However, the basic compounds to be generated by these compounds through irradiation with active energy rays are primary or secondary amines having a low degree of basicity, and are therefore insufficient for fully curing epoxy resin. As a photobase generator capable of photochemically generating tertiary amines having a larger degree of basicity, aromatic aminimide compounds have been reported (Patent Documents 4, 5); and some cases have been reported in which the thermal curing onset temperature is low after irradiation with active energy rays in addition reaction of an epoxy resin and a polythiol compound or the like.

However, these aromatic aminimide compounds require a high temperature in thermal curing therewith, and the thermal curing temperature thereof after irradiation with active energy rays is not still sufficiently low.

BACKGROUND ART

Patent Document

Patent Document 1: EP 599571
Patent Document 2: EP 555749
Patent Document 3: JP-A-4-330444
Patent Document 4: WO2002/051905
Patent Document 5: JP-A-2003-26772

Non-Patent Document

Non-Patent Document 1: Chemistry & Technology of UV & EB Formulation for Coatings, Inks& Paints, Ed. by G. Bradley, John Wiley and Sons Ltd. (1998, p479-p545)
Non-Patent Document 2: J. Org. Chem., 55, 5919 (1990)
Non-Patent Document 3: Polym. Mat. Sci. Eng., 64, 55 (1991)
Non-Patent Document 4: Macromol., 28, 365 (1995)
Non-Patent Document 5: Pure and Appl. Chem., 64, 1239 (1992)

SUMMARY OF THE INVENTION

Problems that the Invention is to Solve

An object of the present invention is to provide a novel aminimide-based thermal/photo-base generator more excellent in low-temperature curability and photoactivity than conventional aminimide-based photobase generators, a curable composition using the generator, which is usable in a reaction system and in other various applications for adhesion, sealing, casting, molding, painting, coating and the like, and which can be cured rapidly at a lower temperature through irradiation with active energy rays, and a curing method for the composition.

Means for Solving the Problems

As a result of assiduous studies to accomplish the object, the inventors have found that a novel aminimide compound having a specific structure can be activated at a lower temperature and can be more active to active energy rays than aminimide compounds heretofore said to be useful mainly as a thermocuring catalyst for epoxy resin, and further can generate a radical with active energy rays, and have completed the present invention.

Specifically, the inventors have found that an aminimide compound (A) having, in the molecule thereof, at least one structure represented by the following general formula (I) is useful as a thermal base generator capable of generating a base at a lower temperature than heretofore-known aminimide compounds, and is useful as a photobase generator having a sufficient active energy ray-based base activity, and is further usable as a photoradical generator that generates a radical with active energy rays, and have completed the present invention.

[Chem. 1]

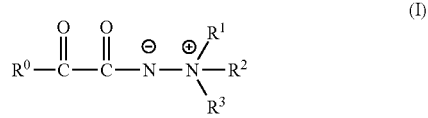

$R^0$ represents a hydrogen atom, an alkyl group which may have an optional substituent, an aryl group which may have an optional substituent, or a heterocyclic residue which may have an optional substituent. $R^1$, $R^2$ and $R^3$ each independently represent a hydrogen atom, or an optional substituent. However, at least two of $R^1$, $R^2$ and $R^3$ may bond to each other to form a cyclic structure.

That is, the present invention relates to the following (1) to (10).

(1) An aminimide compound comprising, in the molecule thereof, a structure represented by the above-mentioned general formula (I).

(2) The aminimide compound according to (1), wherein $R^0$ in the above-mentioned general formula (I) is an aryl group which may have an optional substituent, or a heterocyclic residue which may have an optional substituent.

(3) A composition comprising: (A) an aminimide compound according to (1) or (2); and (B) a compound to be polymerized by a radical and/or a base.

(4) The composition according to (3), wherein the (B) compound to be polymerized by a base is a compound having at least two epoxy groups in the molecule thereof.

(5) The composition according to (3), wherein the (B) compound to be polymerized by a base is a mixture of a compound having at least two epoxy groups in the molecule thereof and a compound having at least two thiol groups in the molecule thereof.

(6) The composition according to (3), wherein the (B) compound to be polymerized by a radical is a compound having at least one ethylenic unsaturated group in the molecule thereof.

(7) The composition according to any one of (3) to (6), which contains the ingredient (A) in an amount of from 0.1 to 50 parts by weight relative to 100 parts by weight of the ingredient (B).

(8) The composition according to (3), further comprising (C) an active energy ray radical generator.

(9) The composition according to (8), which contains the ingredient (A) in an amount of from 0.1 to 50 parts by weight relative to 100 parts by weight of the ingredient (B), and contains the ingredient (C) in an amount of from 0.01 to 10 parts by weight relative to 1 part by weight of the ingredient (A).

(10) A method for curing the composition according to (3) to (9), the method comprising subjecting the composition to heating or irradiation with active energy rays, or to both heating and irradiation with active energy rays simultaneously, or to irradiation with active energy rays followed by heating.

Advantage of the Invention

The present invention relates to a novel aminimide compound having an excellent base generating ability under heat at a lower temperature than before, and an excellent base generating ability with active energy rays, and having also a radical generating ability with active energy rays, provides an active energy ray-polymerizable composition capable of rapidly curable at a lower temperature through heating or/and irradiation with active energy rays, and a curing method for the composition and a cured product, and is usable in various applications of adhesion, sealing, casting, molding, painting, coating, etc.

When the novel aminimide compound is used as a curing catalyst and is combined with, for example, an epoxy resin or the like, the composition may be given thermal curability and additionally curability through irradiation with active energy rays.

BRIEF DESCRIPTION OF THE DRAWINGS

FIG. 1 is a differential scanning calorimetry (DSC) chart of the compositions of Example 27 and Comparative Example 5 before and after irradiation with active energy rays in a cumulative light intensity of 3 J/cm$^2$. It is known that, in both cases before and after irradiation with active energy rays, the composition of the invention started the reaction and finished the reaction at a lower temperature and in a shorter period of time than the Comparative Example.

MODE FOR CARRYING OUT THE INVENTION

The invention is described in detail hereinunder. One embodiment of the present invention is a base generator that generates a base through heating or/and irradiation with active energy rays, and is an aminimide compound having a structure represented by the following general formula (I) in the molecule thereof.

[Chem. 2]

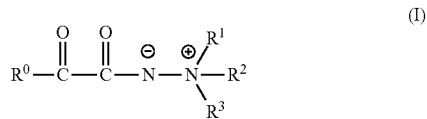

$R^0$ represents a hydrogen atom, an alkyl group which may have an optional substituent, an aryl group which may have an optional substituent, or a heterocyclic residue which may have an optional substituent. $R^1$, $R^2$ and $R^3$ each independently represent a hydrogen atom, or an optional substituent. However, at least two of $R^1$, $R^2$ and $R^3$ may bond to each other to form a cyclic structure.

$R^0$ in the above-mentioned general formula (I) is preferably an aryl group which may have an optional substituent or a heterocyclic residue which may have an optional substituent. When $R^0$ has these structures, then the aminimide compound can have a high activity.

Further, $R^0$ in the general formula (I) is more preferably an aryl group which may have an optional substituent. When $R^0$ has such a structure, then the aminimide compound can have a high photoactivity.

In —N+R$^1$R$^2$R$^3$ in the above-mentioned general formula (I), the cyclic structure to be formed by at least two of $R^1$, $R^2$ and $R^3$ bonding to each other includes 3- to 7-membered hetero rings. The hetero rings include aromatic rings and saturated rings.

As the optional substituent, there may be mentioned single groups of hydroxy, halogen, linear or branched alkyl, cycloalkyl, aryl, benzoyl, benzyl, alkoxy, vinyl, ester, carboxy, aldehyde, amino, imino, imide, nitrile, amide, imido, cyano, sulfo, sulfide, thiol, isocyanate and nitro, or groups formed by combining a plurality of those groups in any desired manner; however, the present invention is not limited thereto. The hetero atom constituting the hetero ring includes N, S, O and the like; however, the present invention is not limited thereto.

For producing the compound having the aminimide structure as above, any known method is employable. For example, as described in Encyclopedia of Polymer Science and Engineering, John Wiley & Sons Ltd. (1985), Vol. 1, p. 740, the compound can be obtained through reaction of a carboxylate, a hydrazine halide and a sodium alkoxide corresponding thereto, or through reaction of a carboxylate, a hydrazine and an epoxy compound. The production method for the aminimide compound (A) for use in the present invention is not specifically limited; however, in consideration of the simplicity and the safety of the production, the production method from a carboxylate, a hydrazine and an epoxy compound is preferred. In that case, the temperature and the time for the production are not specifically limited; but in general, the intended aminimide structure-having compound can be obtained by stirring at a temperature of from 0 to 100° C. for 30 minutes to 7 days. Preferably, the aminimide compound of the present invention is characterized in that its thermal decomposition temperature is lower than that of existing known aminimide compounds, and therefore, it is desirable that the temperature in the initial stage of reaction is controlled to fall within a range of from 0 to 250° C. and the temperature in the final stage is controlled to be not higher than 60° C., for the purpose of inhibiting side reaction and for the purpose of inhibiting thermal decomposition of the formed aminimide.

The carboxylate to be used as the raw material in this production method for the aminimide compound of the present invention may be a monofunctional or polyfunctional compound having a structure of —C—C(O)—C(O)O— in the molecule thereof. For example, there may be mentioned methyl benzoylformate, ethyl benzoylformate, methyl 4-nitrobenzoylformate, methyl 4-methoxybenzoylformate, ethyl 4-methoxybenzoylformate, ethyl 4-n-butylbenzoylformate, ethyl 4-t-butylbenzoylformate, ethyl 3,4-dimethoxybenzoylformate, ethyl 4-isopropylbenzoylformate, ethyl 4-dimethylaminobenzoylformate, ethyl 3,4-dimethylbenzoylformate, ethyl 3-methylbenzoylformate, ethyl 4-methylbenzoylformate, ethyl 4-henoxybenzoylformate, ethyl 4-thiomethylbenzoylformate, ethyl 4-cyanobenzoylformate, methyl pyruvate, ethyl pyruvate, methyl 2-oxovalerate, dimethyl 2-oxoglutarate, ethyl 2-oxo-4-phenylbutyrate, etc., to which, however, the present invention is not limited.

Above all, it is preferred to use a polyfunctional ester compound because an aminimide compound having multiple aminimide structures in the molecule thereof can be obtained.

Not specifically limited, the hydrazine compound to be the raw material for use in the above-mentioned production method for the aminimide compound of the present invention includes, for example, 1,1-dimethylhydrazine, 1-benzyl-1-phenylhydrazine, 1-butyl-1-phenylhydrazine, 1-ethyl-1-phenylhydrazine, 1-methyl-1-phenylhydrazine, 1-aminopyrrolidine, 1-amino-homopiperidine, etc., to which, however, the present invention is not limited. Of those, 1,1-dimethylhydrazine is preferred, in view of the easy availability of the raw compound and of the high degree of the basicity of the photobasic substance to be generated.

The epoxy compound to be the raw material for use in the above-mentioned production method for the aminimide compound of the present invention may be a compound having at least one epoxy group in the molecule thereof. For example, herein usable are monofunctional epoxy compounds such as propylene oxide, glycidol, allyl glycidyl ether, 2-ethylhexyl glycidyl ether, phenyl glycidyl ether, tert butyl phenol glycidyl ether, glycidyl methacrylate, etc.; and in addition thereto, polyfunctional epoxy compounds, such as so-called epi-bis liquid epoxy resins, e.g., resorcinol diglycidyl ether, neopentyl diglycidyl ether, glycerol polyglycidyl ether, diglycidyl ether derived from bisphenol A and epichlorohydrin, etc., polyglycidyl ethers derived from aliphatic/aromatic alcohol and epichlorohydrin, polyglycidyl esters derived from polybasic acid and epichlorohydrin, polyglycidyl ethers derived from hydrogenated bisphenol A and epichlorohydrin, etc. By changing the structure of the epoxy compound, the solubility, the crystallinity, the volatility or the like of the aminimide compound to be obtained and the base to be generated through heating thereof and/or irradiation thereof with active energy rays can be controlled. It is preferred to use a polyfunctional epoxy compound because an aminimide compound having multiple aminimide structures in the molecule thereof can be obtained.

The aminimide compound (A) of the present invention is decomposed by heating at a lower temperature than before to generate a base, and is therefore effective as a catalyst or a retardant in a reaction system where the reaction speed varies depending on a basic substance. In addition, the compound generates a base through irradiation with active energy rays, and is therefore also effective as a photoactive catalyst or a retardant in a reaction system where the reaction speed varies depending on a basic substance. Further, the compound also generates a radical through irradiation with active energy rays, and is therefore effective as a photoactive catalyst or a retardant in a reaction system where the reaction speed varies depending on a radical. In one embodiment of the present invention, the above-mentioned aminimide compound (A) is mixed with a compound (B) to be polymerized by a radical and/or a base, thereby giving a curable composition.

The compound to be polymerized by a radical and/or a base (B) includes known compounds capable of being polymerized by a base or known compounds capable of being polymerized by a radical, to which, however, the present invention is not limited.

"Polymerization" for the known compounds capable of being polymerized by a base includes, for example, Michael addition reaction, homopolymerization of an epoxy compound with a basic catalyst, polymerization of at least one selected from epoxy compounds, (meth)acrylate compounds and episulfide compounds and a compound containing at least one selected from thiol, amino, phenol, isocyanate, carboxyl and acid anhydride groups, polymerization of a hydroxy and/or thiol group-containing compound and an isocyanate-containing compound, homopolymerization of a compound having a silicon-containing group and capable of being polymerized by forming a siloxane bond therein, homopolymerization of a cyanoacrylate group-having compound, etc., to which, however, the present invention is not limited.

In case where a cured product is obtained by the use of the aminimide compound of the present invention, it is preferred to use an epoxy resin, a composition containing an epoxy resin as the main ingredient thereof, or a composition containing an epoxy resin or a polythiol compound as the main ingredient thereof as the compound (B) to be polymerized by a base, to which, however, the present invention is not limited.

The compound (B) to be polymerized by a radical includes a monomer or an oligomer having at least one ethylenic unsaturated group in the molecule thereof, such as methyl (meth)acrylate, ethyl (meth)acrylate, hydroxyethyl (meth) acrylate, 2-(meth)acryloyloxyethyl hexahydrophthalate, cyclohexyl (meth)acrylate, dicyclopentanyl (meth)acrylate, dicyclopentenyl (meth)acrylate, isobornyl (meth)acrylate, (meth)acryloylmorpholine, imide (meth)acrylate, glycidyl (meth)acrylate, etc.; to which, however, the present invention is not limited. One or more of these compounds may be used here either singly or as combined.

The blending quantity of the aminimide compound (A) in the composition of the invention varies depending on the type of the compound (B) to be polymerized by a radical and/or a base; and for example, in case where an epoxy resin is selected as the ingredient (B), the quantity is preferably from 0.1 to 50 parts by weight relative to 100 parts by weight of the epoxy resin, more preferably from 0.1 to 30 parts by weight. When the quantity is more than 50 parts by weight, the characteristics such as heat resistance, strength and the like of the cured product may worsen.

The epoxy resin preferably used here as the ingredient (B) includes a compound having at least two epoxy groups in the molecule thereof, and specific examples thereof include so-called epi-bis liquid epoxy resins, such as diglycidyl ethers to be derived from bisphenol A and epichlorohydrin, and their derivatives, diglycidyl ethers to be derived from bisphenol F and epichlorohydrin, and their derivatives, etc.; phenol-novolak epoxy resins, cresol-novolak epoxy resins, hydantoin epoxy resins, isocyanurate epoxy resins; glycidyl ethers to be derived from aliphatic/aromatic alcohol and epichlorohydrin, glycidyl esters to be derived from polybasic acid and epichlorohydrin, and their derivatives; hydrogenated glycidyl ethers to be derived from bisphenol A and epichlorohydrin, aliphatic cyclic epoxy such as 3,4-epoxy-6-methylcyclohexylmethyl-3,4-epoxy-6-methylcyclohexane carboxylate, bis(3,4-epoxy-6-methylcyclohexylmethyl) adipate, etc., and their derivatives; 5,5'-dimethylhydantoin epoxy resins, triglycidyl isocyanates, substituted epoxy to be derived from isobutylene, etc.; however, the present invention is not limited thereto. Commercially-available epoxy resin products are also usable here, including, for example, Japan Epoxy Resin's JER 828, 1001, 801, 806, 807, 152, 604, 630, 871, YX 8000, YX 8034, YX 4000; Dai-Nippon Ink Industry's Epiclon 830, 850, 830 LVP, 850 CRP, 835 LV, HD 4032D, 703, 720, 726, HP820; Asahi Denka Industry's EP 4100, EP 4000, EP 4080, EP 4085, EP 4088, EPU 6, EPR 4023, EPR 1309, EP 49-20; Nissan Chemical Industry's TEPIC; Shin-Etsu Chemical Industry's KF-101, KF-1001, KF-105, X-22-163B, X-22-9002, Nagase Chemtex's Denacol EX411, EX314, EX201, EX212, EX252, etc.; however, the present invention is not limited thereto. These compounds may be used here either singly or as a mixture of two or more of them. Of those, use of epi-bis epoxy resins gives well-balanced compositions advantageous in point of the cost and the curability thereof and the adhesiveness and the physical strength of the curd products, etc. Use of aliphatic or cyclic aliphatic epoxy compounds gives compositions excellent in the softness, the transparency and the weather resistance of the cured products.

The polythiol compound that may be combined with the epoxy resin may be any and every compound having at least two thiol groups in the molecule thereof. Specific examples thereof include trimethylolpropane tristhiopropionate, pentaerythritol tetrakis(3-mercaptopropionate), ethylene glycol bisthioglycolate, 1,4-butanediol bisthioglycolate, trimethylolpropane tristhioglycolate, pentaerythritol tetrakisthioglycolate, di-(2-mercaptoethyl)ether, 1,4-butanedithiol, tris[(3-mercaptopropionyloxy)-ethyl] isocyanurate, 1,3,5-trimercaptomethylbenzene, 4,4'-thiodibenzenethiol, 1,3,5-trimercaptomethyl-2,4,6-trimethylbenzene, 2,4,6-trimercapto-s-triazine, 2-dibutylamino-4,6-dimercapto-s-triazine, terminal thiol group-having polyether, terminal thiol group-having polythioether, thiol compound to be obtained through reaction of epoxy compound and hydrogen sulfide, terminal thiol group-having thiol compound to be obtained through reaction of polythiol compound and epoxy compound, etc.; however, the present invention is not limited thereto. Commercially-available thiol compounds are also usable here, including, for example, Japan Epoxy Resin's JER Mate QX11, QX12, JER Cure QX30, QX40, QX60, QX900, Capcure CP3-800; Sakai Chemical Industry's TMMP, PEMP, DPMP, TEMPIC; Yodo Chemical's OTG, EGTG, TMTG, PETG, 3-MPA, TMTP, PETP; Shin-Etsu Chemical Industry's KF-2001, KF-2004, X-22-167B; Toray Fine Chemical's Thiokol LP-2, LP-3, Polythiol QE-340M, etc.; however, the present invention is not limited thereto. These compounds may be used here either singly or as a mixture of two or more of them. Thiol compounds in which the content of basic impurities is as small as possible are preferred from the viewpoint of the storage stability thereof. On the other hand, from the viewpoint of the heat resistance of the cured products, more preferred are thiol compounds containing an aromatic ring or an isocyanurate ring in the molecule thereof. The content of the thiol compound to be in the composition of the present invention is not specifically defined, but preferably, the content is within a range of from 0.5 to 2.0 in terms of the thiol equivalent ratio relative to the epoxy equivalent of the epoxy compound in the composition, more preferably within a range of from 0.8 to 1.3. Adding a thiol compound within the above-mentioned range gives well-balanced compositions excellent in the curing speed and the balance of the strength and the heat resistance of the cured products.

In the present invention, preferably, an active energy ray radical generator (C) is further added to the composition comprising the above-mentioned ingredients (A) and (B) as the main ingredients thereof, as the radical curability of the composition and the base generating efficiency with active energy rays thereof may be further enhanced. As the active energy ray radical generator, well-known hydrogen-drawing radical generators or/and cleavage radical generators are able to use. Examples of the hydrogen-drawing radical generator include naphthalene derivatives such as 1-methylnaphthalene, 2-methylnaphthalene, 1-fluoronaphthalene, 1-chloronaphthalene, 2-chloronaphthalene, 1-bromonaphthalene, 2-bromonaphthalene, 1-iodonaphthalene, 2-iodonaphthalene, 1-naphthol, 2-naphthol, 1-methoxynaphthalene, 2-methoxynaphthalene, 1,4-dicyanonaphthalene, etc.; anthracene derivatives such as anthracene, 1,2-benzanthracene, 9,10-dichloroanthracene, 9,10-dibromoanthracene, 9,10-diphenylanthracene, 9-cyanoanthracene, 9,10-dicyanoanthracene, 2,6,9,10-tetracyanoanthracene, etc.; pyrene derivatives; carbazole derivatives such as carbazole, 9-methylcarbazole, 9-phenylcarbazole, 9-propen-2-yl-9H-carbazole, 9-propyl-9H-carbazole, 9-vinylcarbazole, 9H-carbazole-9-ethanol, 9-methyl-3-nitro-9H-carbazole, 9-methyl-3,6-dinitro-9H-carbazole, 9-octanoylcarbazole, 9-carbazole-methanol, 9-carbazole-propionic acid, 9-carbazole-propionitrile, 9-ethyl-3,6-dinitro-9H-carbazole, 9-ethyl-3-nitrocarbazole, 9-ethylcarbazole, 9-isopropylcarbazole, 9-(ethoxycarbonylmethyl)carbazole, 9-(morpholinomethyl)carbazole, 9-acetylcarbazole, 9-allylcarbazole, 9-benzyl-9H-carbazole, 9-carbazole-acetic acid, 9-(2-nitrophenyl)carbazole, 9-(4-methoxyphenyl)carbazole, 9-(1-ethoxy-2-methylpropyl)-9H-carbazole, 3-nitrocarbazole, 4-hydroxycarbazole, 3,6-dinitro-9H-carbazole, 3,6-diphenyl-9H-carbazole, 2-hydroxycarbazole, 3,6-diacetyl-9-ethylcarbazole, etc.; benzophenone derivatives such as benzophenone, 4-phenylbenzophenone, 4,4'-bis(dimethoxy) benzophenone, 4,4'-bis(dimethylamino)benzophenone, 4,4'-bis(diethylamino)benzophenone, methyl ester 2-benzoylbenzoate, 2-methylbenzophenone, 3-methylbenzophenone, 4-methylbenzophenone, 3,3'-dimethyl-4-methoxybenzophenone, 2,4,6-trimethylbenzophenone, etc.; aromatic carbonyl compounds; [4-(4-methylphenylthio) phenyl]-phenylmethanone, xanthone; thioxanthone derivatives such as thioxanthone, 2-chlorothioxanthone, 4-chlorothioxanthone, 2-isopropylthioxanthone, 4-isopropylthioxanthone, 2,4-dimethylthioxanthone, 2,4-diethylthioxanthone, 1-chloro-4-propoxythioxanthone, etc.; coumarin derivatives.

Furthermore, the cleavage radical generator is a radical generator of a type that generates a radical through cleavage of the compound as a result of irradiation with active energy rays. Specific examples of the generator of the type include benzoin ether derivatives; aryl alkyl ketones such as acetophenone derivatives; oxime ketones, acylphosphine oxides, S-phenyl thiobenzoates; titanocenes; and their derivatives produced through polymerization of the compounds; however, the present invention is not limited thereto. Commercially-available cleavage radical generators usable here include 1-(4-dodecylbenzoyl)-1-hydroxy-1-methylethane, 1-(4-isopropylbenzoyl)-1-hydroxy-1-methylethane, 1-benzoyl-1-hydroxy-1-methylethane, 1-[4-(2-hydroxyethoxy)-benzoyl]-1-hydroxy-1-methylethane, 1-[4-(acryloyloxyethoxy)-benzoyl]-1-hydroxy-1-methylethane, diphenyl ketone, phenyl-1-hydroxy-cyclohexyl ketone, benzyldimethyl ketal, bis(cyclopentadienyl)-bis(2,6-difluoro-3-pyrrylphenyl)titanium, (6-isopropylbenzene)-(5-cyclopentadienyl)-iron(II) hexafluorophosphate, trimethylbenzoyldiphenylphosphine oxide, bis(2,6-dimethoxy-benzoyl)-(2,4,4-trimethyl-pentyl)phosphine oxide, bis(2,4,6-trimethylbenzoyl)-2,4-dipentoxyphenylphosphine oxide or bis(2,4,6-trimethylbenzoyl)phenylphosphine oxide, (4-morpholinobenzoyl)-1-benzyl-1-dimethylaminopropane, 4-(methylthiobenzoyl)-1-methyl-1-morpholinoethane and 2-hydroxy-2-methyl-1-phenyl-propan-1-one, etc.; however, the present invention is not limited thereto.

In the composition of the present invention, the active energy ray radical generator (C), or that is, the hydrogen-drawing or cleavage radical generator of those compounds may be used either singly or as a mixture of two or more of them. A polymer-type radical generator produced by introducing a structure of the radical generator into a high-molecular oligomer/polymer is preferred here, as producing little gas during and after curing.

Depending on the type of the radical generator and on the structure of the aminimide compound (A) to be combined with the radical generator, there may occur a difference in the effect of the radical generator; and therefore, the most suitable combination of the aminimide compound (A) and the radical generator (C) may be selected appropriately in any desired manner. The amount of the radical generator to be added to the composition of the present invention must be determined in consideration of the absorption wavelength and the molar extinction coefficient of the radical generator; however, in general, the amount of the radical generator may be from 0.01 to 10 parts by weight relative to 1 part by weight of the aminimide compound (A), preferably from 0.05 to 5 parts by weight. When the amount is too small, then the base generation efficiency could not be enhanced in irradiation with active energy rays; but when too large, the generator may interfere with the effect of the basic catalyst.

A compound having at least one epoxy group in the molecule thereof and/or a compound having at least one thiol group in the molecule thereof may be added to the composition of the present invention, within a range not detracting from the characteristic features of the present invention. The compounds can serve for reducing the viscosity of the composition, for enhancing the workability thereof, and for controlling the reactivity thereof. When the epoxy compound and the thiol compound is added, preferably, the blending quantity of the epoxy compound and the thiol compound in the entire composition is controlled in consideration of the epoxy equivalent and the thio equivalent of the compound to be added.

Also within a range not detracting from the characteristic features of the present invention, additives may be added to the composition of the present invention. The additives include colorants such as pigment, dye, etc.; inorganic fillers such as calcium carbonate, talc, silica, alumina, aluminium hydroxide, etc.; electroconductive particles of silver, etc.; flame retardants; storage stability enhancers such as borate ester, phosphate, inorganic acids, organic acids, etc.; organic fillers such as acrylic rubber, silicone rubber, etc.; polymers and thermoplastic elastomers such as polyimide resins, polyamide resins, general-purpose phenoxy resins, e.g., bisphenol A-type phenoxy resins, bisphenol F-type phenoxy resins, bisphenol A/bisphenol F copolymer-type phenoxy resins, etc., polymethacrylate resins, polyacrylate resins, polyimide resins, polyurethane resins, polyester resins, polyvinyl butyral resins, SBS resins and their epoxy resin-modified derivatives, SEBS resins and their modified derivatives, etc.; additives such as plasticizers, organic solvents, non-reactive diluents, reactive diluents, antioxidants, curing promoters, sensitizers, light stabilizers, heavy metal inactivators, ion-trapping agents, emulsifiers, aqueous dispersion stabilizers, defoaming agents, release agents, coupling agents, leveling agents, waxes, rheology-controlling agents, etc. Adding the additives gives a composition and its cured products excellent in resin strength, adhesion strength, flame retardancy, heat conductivity, storage stability, workability, etc. Commercially-available storage stability improvers usable here are Johoku Chemical Industry's JP-3CP, JPP-31, JPA-514; Shikoku Chemical Industry's L-07N, etc.; however, the present invention is not limited thereto.

The aminimide compound (A) of the present invention is activated through heating and/or irradiation with active energy rays to generate a base and/or a radical, but the active energy rays include electron rays, visible rays, UV rays, etc. Of those, preferred in the present invention are visible rays and UV rays, not requiring any specific apparatus and easy to use. Not specifically limited, the quantity of the active energy rays to be radiated may be on a level satisfactory for curing. In one example where an epoxy resin is used as the ingredient (B), the radiation dose of the active energy rays may be at least 0.1 J/cm$^2$. When exposed to both irradiation with active energy rays and heating, the composition of the present invention may give a cured product within a shorter period of time, requiring a further smaller radiation dose of active energy rays.

The aminimide compound (A) of the present invention may be activated only by heating at a lower temperature than before; however, as compared with activation of the compound by heating alone, activation thereof by the combination of heating and irradiation with active energy rays can greatly enhance the curability of the composition. In an ordinary UV radiation apparatus, heat rays are radiated along with UV rays, and therefore it is extremely useful for curing the composition of the present invention.

The cured product of the composition of the present invention has excellent characteristic features of toughness and transparency; and the composition of the present invention irradiated with a predetermined amount of active energy rays can cure to give a cured product only when left at room temperature, not requiring any specific post-treatment (such as heating, etc.). Taking advantage of the characteristic features, the composition can be used in various applications of shaping into optical members, as well as for adhesives, sealants, casting, painting, coating, etc. Also, in the composition within the present invention, the composition of the present invention can cure directly after irradiation with active energy rays, or does not cure immediately after irradiation with active energy rays but may cure after left for while at room temperature or under heat; and the latter property of the composition makes it possible to use the composition as an adhesive such as typically an adhesive for DVD, with which even though the parts to be adhered are impervious to active energy rays, the parts can be adhered together by sticking to each other after the composition to be applied thereto has been irradiated with active energy rays.

Furthermore, in the composition within the present invention, the radical-curable ingredient can be cured through irradiation with active energy rays, and thereafter while left at room temperature or under heat, the base-curable ingredient therein can be cured. The property of the composition makes it possible to use the composition in various applications that require provisional fixation and shape retention through irradiation with active energy rays and adhesion through the subsequent heating process.

EXAMPLES

The invention is described concretely with reference to the following Examples; however, the present invention is not limited by these Examples. Unless otherwise specifically indicated, the blending ratio in the following Tables is by weight.

The aminimide compounds used in Examples and Comparative Examples are the compounds having the structural formula shown in Table 1, and these were produced according to the methods mentioned below.

TABLE 1

| | | |
|---|---|---|
| Example 1 | Aminimide Compound A | 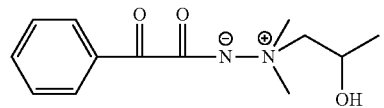 [SMILES: CC(O)C[N+](C)(C)[N-]C(=O)C(=O)c1ccccc1] |
| Example 2 | Aminimide Compound B | 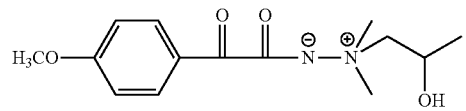 [SMILES: COc1ccc(C(=O)C(=O)[N-][N+](C)(C)CC(C)O)cc1] |
| Example 3 | Aminimide Compound C | 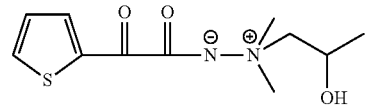 |
| Example 4 | Aminimide Compound D | 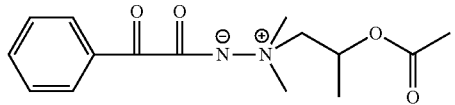 |
| Example 5 | Aminimide Compound E | 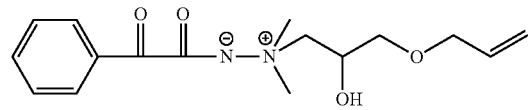 [SMILES: C=CCOCC(O)C[N+](C)(C)[N-]C(=O)C(=O)c1ccccc1] |
| Example 6 | Aminimide Compound F | 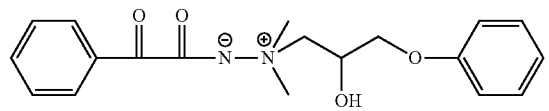 [SMILES: C[N+](C)(CC(O)COc1ccccc1)[N-]C(=O)C(=O)c1ccccc1] |
| Comparative Example 1 | Aminimide Compound G | 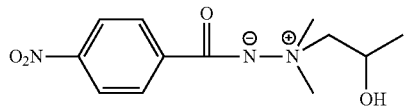 [SMILES: CC(O)C[N+](C)(C)[N-]C(=O)c1ccc([N+](=O)[O-])cc1] |

Example 1

Synthesis of Aminimide Compound A 13.6 g (83.0 mmol) of methyl benzoylformate, 4.80 g (83.0 mmol) of propylene oxide and 5.00 g (83.0 mmol) of 1,1-dimethylhydrazine (all Tokyo Chemical Industry's reagents) were put into a 200-ml brown eggplant flask, to which 80 ml as a solvent, isopropyl alcohol (Kokusan Chemical's reagent) had been put, and sealed up and shielded from light, then stirred at 20° C. for 2 hours, and further stirred at 40° C. for 2 days. Increase in the aminimide carbonyl absorption wavelength in IR measurement confirmed the generation of aminimide. Solvent removal under reduced pressure gave a white crystal. This was recrystallized in a mixed solution of methanol and ethyl acetate to give 19.7 g of a crystal of the aminimide compound A (yield 95%). This was recrystallized further twice with a mixed solution of methanol and ethyl acetate for purification.

Melting point: 104-105° C. (decomposition)
IR (C=O): 1681 $cm^{-1}$, 1571 $cm^{-1}$
Elementary analysis of $C_{13}H_{18}N_2O_3$ (elementary analyzer, LECO's CHNS-932 Model and VTF-900 Model):
Calculated value: C, 62.38%; H, 7.25%; N, 11.19%; O, 19.18%.
Measured value: C, 62.30%; H, 7.17%; N, 11.28%; O, 18.94%.

Example 2

Synthesis of Aminimide Compound B 3.7 g of a crystal of the aminimide compound B was obtained in the same manner as that for the production of the aminimide compound A, except that 3.54 g (17.0 mmol) of ethyl 4-methoxybenzoylformate (Oakwood Products' reagent), 0.99 g (17.0 mmol) of propylene oxide (Tokyo Chemical Industry's reagent) and 1.02 g (17.0 mmol) of 1,1-dimethylhydrazine (Tokyo Chemical Industry's reagent) were put into a 100-ml brown eggplant flask, to which 30 ml as a solvent, isopropyl alcohol (Kokusan Chemical's reagent) had been put (yield 78%). This was recrystallized further twice with a mixed solution of methanol and ethyl acetate for purification. Increase in the aminimide carbonyl absorption wavelength in IR measurement confirmed the formation of aminimide.

Melting point: 102-103° C. (decomposition)
IR (C=O): 1670 $cm^{-1}$, 1578 $cm^{-1}$
Elementary analysis of $C_{14}H_{20}N_2O_4$ (elementary analyzer, LECO's CHNS-932 Model and VTF-900 Model):
Calculated: C, 59.99%; H, 7.19%; N, 9.99%; O, 22.83%.
Found: C, 60.00%; H, 6.98%; N, 10.00%; O, 22.84%.

Example 3

Synthesis of Aminimide Compound C 4.7 g of a crystal of the aminimide compound Addition 1 was obtained in the same manner as that for the production of the aminimide compound A, except that 3.68 g (20.0 mmol) of ethyl-thiophene-2-glyoxylate (Alfa Aecar's reagent), 1.16 g (20.0 mmol) of propylene oxide (Tokyo Chemical Industry's reagent) and 1.20 g (20.0 mmol) of 1,1-dimethylhydrazine (Tokyo Chemical Industry's reagent) were put into a 50-ml brown eggplant flask, to which 30 ml of a solvent, isopropyl alcohol (Kokusan Chemical's reagent) had been put (yield 93%). This was recrystallized further twice with a mixed solution of methanol and ethyl acetate for purification. Increase in the aminimide carbonyl absorption wavelength in IR measurement confirmed the formation of aminimide.

Melting point: 119-120° C. (decomposition)
IR (C=O): 1651 $cm^{-1}$, 1574 $cm^{-1}$

Example 4

Synthesis of Aminimide Compound D 3.00 g of the aminimide compound A, 2.45 g of acetic anhydride (Tokyo Chemical Industry's reagent) and 1.21 g of triethylamine (Tokyo Chemical Industry's reagent) were put into a 100-ml brown eggplant flask, to which 30 ml as a solvent, dichloromethane (Tokyo Chemical Industry's reagent) had been put, and stirred under reflux for 24 hours. The solvent and the remaining raw materials were removed under reduced pressure, and the resulting paste was washed with normal hexane to give a white solid. The solid was recrystallized with ethyl acetate to give 1.80 g of a crystal of the aminimide compound D (yield 51.8%). This was recrystallized further twice with ethyl acetate for purification.

Melting point: 100-101° C. (decomposition)
IR (C=O): 1740 $cm^{-1}$, 1681 $cm^{-1}$, 1604 $cm^{-1}$
Elementary analysis of $C_{15}H_{20}N_2O_4$ (elementary analyzer, LECO's CHNS-932 Model):
Calculated value: C, 61.63%; H, 6.90%; N, 9.58%.
Measured value: C, 61.59%; H, 7.13%; N, 9.55%.

Example 5

Synthesis of Aminimide Compound E 4.92 g (30.0 mmol) of methyl benzoylformate, 3.42 g (30.0 mmol) of allyl glycidyl ether (Kanto Chemical's reagent) and 1.80 g (30.0 mmol) of 1,1-dimethylhydrazine (Tokyo Chemical Industry's reagent) were put into a 50-ml brown eggplant flask, to which 30 ml of isopropyl alcohol (Kokusan Chemical's reagent) as a solvent, had been put, and sealed up, shielded from light, and stirred at 25° C. for 7 days. Increase in the aminimide carbonyl absorption wavelength in IR measurement confirmed the formation of aminimide. The solvent was removed under reduced pressure, and the residue was washed with normal hexane and dried under reduced pressure to give 9.1 g of a pale yellow viscous liquid (yield 98%).

IR (C=O): 1677 $cm^{-1}$, 1588 $cm^{-1}$

Example 6

Synthesis of Aminimide Compound F 2.79 g (17.0 mmol) of methyl benzoylformate, 2.55 g (17.0 mmol) of phenyl glycidyl ether (Kanto Chemical's reagent) and 1.02 g (17.0 mmol) of 1,1-dimethylhydrazine (Tokyo Chemical Industry's reagent) were put into a 50-ml brown eggplant flask, to which 30 ml of isopropyl alcohol (Kokusan Chemical's reagent) as a solvent, had been put, and sealed up, shielded from light, and stirred at 25° C. for 10 days. Increase in the aminimide carbonyl absorption wavelength in IR measurement confirmed the formation of aminimide. The solvent was removed under reduced pressure, and the residue was washed with normal hexane and dried under reduced pressure to give 5.7 g of a pale yellow viscous liquid (yield 98%).

IR (C=O): 1670 $cm^4$, 1593 $cm^{-1}$

Comparative Example 1

Synthesis of Aminimide Compound G

According to the method disclosed in J. Polym. Sci. Part A: Polym. Chem., 35, 689, (1997) and WO2002/051905, the aminimide compound G not to be included in the present invention was obtained from the corresponding methyl carboxylate, 1,1-dimethylhydrazine and epoxy compound.

Melting point: 155° C.
IR (C=O): 1585 cm$^{-1}$

Example 7

Confirmation of Photobase Generation

An aqueous solution having a concentration of 1.00 g/L was prepared from the aminimide compound A and pure water, and 50 ml of this was put into a transparent glass-made sample bottle having an inner diameter of 38 mm and a height of 58 mm, and with stirring with a stirrer while sealed up, the pH of the aqueous solution was measured with a pH meter, Horiba Seisakusho's D54. Further kept sealed up, the sample bottle was irradiated with 365-nm active energy rays on the side thereof at a lighting intensity of 100 mW/cm$^2$, using a spot UV irradiator, Hamamatsu Photonics' LC8, and the pH of the solution was measured after irradiation for specified seconds. The pH before irradiation with active energy rays was 6.28; and the pH after irradiation with active energy rays for 20 seconds was 9.78; the pH after irradiation for 30 seconds was 9.90; and the pH after irradiation for 50 seconds was 10.01. In that manner the basicity increased through irradiation with active energy rays, indicating that the aminimide compound A is a photobase generator.

Examples 8 to 12 and Comparative Example 2

Confirmation of Photoradical Generation

In the ratio by weight shown in Table 2, the materials were dissolved by stirring in a light-resistant container at 25° C., thereby preparing acrylate compositions of Examples 8 to 12 and Comparative Example 2. 0.05 g of the composition was dropped onto a slide glass, and irradiated with active energy rays in an accumulated quantity of light, 6 J/cm$^2$, using a spot UV irradiator, Hamamatsu Photonics' LC8 (365 nm intensity, 100 mW/cm$^2$). All the compositions of Examples 8 to 12 cured after irradiation with UV rays. On the other hand, the composition not containing the aminimide compound of the present invention did not cure, which indicates that the aminimide compound of the present invention has the ability to generate a radical with active energy rays and to cure an acrylate compound.

Epiclon EXA-835LV: DIC's high-purity bisphenol-type epoxy resin
Epiclon EXA-850CRP: DIC's high-purity bisphenol A-type epoxy resin
Adeka Resin EP-4085S: ADEKA's aliphatic epoxy resin
Pentaerythritol tetrakis(3-mercaptopropionate): Sigma Aldrich Japan's reagent (hereinafter abbreviated as PEMP)
JER Cure QX30: Japan Epoxy Resin's trifunctional aliphatic polythiol
Darocure 1173 (2-hydroxy-2-methyl-1-phenyl-propan-1-one): Ciba Specialty Chemical's cleavage photoradical generator
Benzophenone: Tokyo Chemical Industry's reagent, hydrogen-drawing photoradical generator
Triethyl borate: Tokyo Chemical Industry's reagent
Benzyl alcohol: Tokyo Chemical Industry's reagent
Aerosil R972: Nippon Aerosil's hydrophobic fumed silica

Preparation of Compositions of Examples 13 to 16 and Comparative Example 3

In the ratio by weight shown in Table 3, the materials were mixed by stirring in a light-resistant container at 50° C. for 10 minutes, thereby uniformly dissolving or uniformly dispersing the aminimide compound to prepare epoxy resin compositions of Examples 13 to 16 and Comparative Example 3. Each of the aminimide compounds solid at room temperature was uniformly ground in a mortar before mixed with the other ingredients.

The obtained compositions were tested and evaluated for the following items, and the results are shown in Table 3. The evaluation test methods are as mentioned below.

Solubility Test of Aminimide Compound:

In the ratio by weight shown in Table 3, the materials were mixed by stirring in a light-resistant container, and visually checked as to whether or not the aminimide compound could be entirely dissolved. The sample in which the compound dissolved at room temperature (25° C.) was shown as "A"; the sample in which the compound dissolved by stirring at 50° C. for 10 minutes was shown as "B"; the sample in which the compound did not dissolve even by stirring at 50° C. for 1 hour was expressed as "not dissolved".

Measurement of Curing Time at 100° C.:

Two slide glasses were stuck together with the composition, left in a constant-temperature furnace set at 100° C., and

TABLE 2

|  | Example 8 | Example 9 | Example 10 | Example 11 | Example 12 | Comparative Example 2 |
| --- | --- | --- | --- | --- | --- | --- |
| Acryester HO (2-hydroxyethyl methacrylate) manufactured by Mitsubishi Rayon | 1 | 1 | 1 | 1 | 1 | 1 |
| Aminimide Compound A | 0.04 |  |  |  |  |  |
| Aminimide Compound B |  | 0.03 |  |  |  |  |
| Aminimide Compound C |  |  | 0.06 |  |  |  |
| Aminimide Compound E |  |  |  | 0.04 |  |  |
| Aminimide Compound F |  |  |  |  | 0.05 |  |
| Solubility of Aminimide Compound | dissolved | dissolved | dissolved | dissolved | dissolved | — |
| Curing through Photoirradiation | cured | cured | cured | cured | cured | not cured |

The materials other than the aminimide compound used in Examples and Comparative Examples are commercially-available products or reagents mentioned below.

the time taken for the composition to cure so that the glasses adhered together and could no more be moved by hand was measured.

Curing Time at 100° C. after Photoirradiation:

50 mg of the composition was taken in a colorless transparent glass-made sample bottle having an inner diameter of 10 mm and a height of 30 mm, and sealed up. At the bottom thereof, the bottle was irradiated with active energy rays in an accumulated quantity of light, 3 J/cm$^2$, using a spot UV irradiator, Hamamatsu Photonics' LC8 (365 nm intensity, 100 mW/cm$^2$). The composition thus irradiated with active energy rays was tested for the curing time at 100° C. in the same manner as above.

Storage Stability at 25° C.:

The composition was put in a light-resistant bottle having a capacity of 15 ml, then sealed up, and stored in a dark, constant-temperature room at 25° C. The time taken by the composition to gel and lose its flowability was measured.

When irradiated with active energy rays in an accumulated quantity of light, 6 J/cm$^2$, the composition cured and gave a rubber-like cured product at room temperature, as observed visually. The glass transition temperature of the cured product was measured with a Seiko Instruments' differential scanning calorimeter (DSC110), and the glass transition point thereof was −2° C. Next, when the composition that had become rubbery through irradiation with active energy rays in an accumulated quantity of light, 6 J/cm$^2$ was heated at 100° C., then it cured in 20 minutes, as observed visually. The glass transition point of the cured product was measured in the same manner as above, and was 71° C.

It is known that the compound of the present invention secures rapid shape retention or provisional fixation through

TABLE 3

|  | Example 13 | Example 14 | Example 15 | Example 16 | Comparative Example 3 |
|---|---|---|---|---|---|
| EXA-835LV | 1 | 1 | 1 | 1 | 1 |
| Aminimide Compound A | 0.145 | | | | |
| Aminimide Compound B | | 0.150 | | | |
| Aminimide Compound E | | | 0.200 | | |
| Aminimide Compound F | | | | 0.190 | |
| Aminimide Compound G | | | | | 0.155 |
| Triethyl Borate | | | 0.005 | 0.005 | |
| Solubility of Aminimide Compound | B | B | A | A | not dissolved |
| 100° C. Curing Time | 60 min | 55 min | 55 min | 60 min | not cured even after 8 hours |
| 100° C. Curing Time after Photoirradiation | 30 min | 30 min | 25 min | 45 min | not tested, as not dissolved |
| 25° C. Storage Stability | one month or more | one month or more | one month or more | one month or more | one month or more |

From Examples 13 to 16, it is known that the aminimide compound of the present invention generates a basic substance at a lower temperature than before and can cure an epoxy resin at 100° C. within a short period of time of 60 minutes or less.

On the other hand, as shown in Comparative Example 3, the composition, to which an aromatic aminimide compound differing from the aminimide compound of the present invention was added, dissolves poorly in the resin and cures poorly at a low temperature, and does not have the ability to cure an epoxy resin at 100° C.

In addition, from Examples 13 to 16, it is known that the composition containing the aminimide compound of the present invention can greatly shorten the heating curing time thereof through irradiation with active energy rays.

Example 17

Combination of Radical Curing and Curing with Base 2.0 g of Epiclon EXA-835LV, 7.0 g of UVACURE 1561 (Daicel-Cytec's acrylic group-having epoxy resin), 0.8 g of 4HBAGE (Nippon Kasei Chemical's 4-hydroxybutyl acrylate glycidyl ether), 0.2 g of Acryester HO (Mitsubishi Rayon's 2-hydroxyethyl methacrylate) and 1.0 g of the aminimide compound A were mixed, and dissolved by stirring at 25° C. to give a composition.

7.5 mg of the composition was dropped into a sample container for differential scanning calorimetry (DSC), and cured with active energy rays under heat. For irradiation with active energy rays, used was a spot UV irradiator Hamamatsu Photonics' LC8 (365 nm intensity, 100 mW/cm$^2$). For heating, a constant-temperature furnace set at 100° C. was used.

irradiation with active energy rays, and that, using the compound, a resin composition can be obtained which can firmly cure by heating.

Examples 18 to 26, and Comparative Example 4

In the ratio by weight shown in Table 4, the materials were uniformly mixed by stirring in a light-resistant container at room temperature (25° C.) or at 40° C. for 10 minutes, thereby preparing epoxy/thiol resin compositions of Examples 18 to 26 and Comparative Example 4. The compositions were tested as follows, and the results are shown in Table 4.

Solubility Test of Aminimide Compound:

In the ratio by weight shown in Table 4, the materials were mixed by stirring in a light-resistant container, and visually checked as to whether or not the aminimide compound could be entirely dissolved. The sample in which the compound dissolved at room temperature (25° C.) was shown as "A"; the sample in which the compound dissolved by stirring at 40° C. for 10 minutes was shown as "B".

Storage Stability at 25° C.:

The composition was put in a glass-made light-resistant bottle having a capacity of 15 ml, then sealed up, and stored in a dark room at 25° C. The time taken by the composition to gel and lose its flowability was measured.

Measurement of Curing Time at 70° C.:

10 mg of the composition was dropped onto the center part of a slide glass, and another slide glass was put over it, whereby the two slide glasses were stuck together. Directly as it was, or after irradiated with active energy rays in an accumulated quantity of light of 6 J/cm$^2$, using an Ushio Electric's conveyor type UV irradiator, this was put in a constant-temperature furnace set at 70° C.; and the time taken for the composition to cure so that the glasses were firmly stuck together and could no more be moved by hand was measured.

Curing Time at 25° C. after Irradiation with Active Energy Rays:

In the same manner as that for the measurement of the 70° C. curing time, two slide glasses were stuck together, then irradiated with active energy rays in an accumulated quantity of light, 6 J/cm$^2$, using an Ushio Electric's conveyor type UV irradiator, and then left in a light-shielded room at 25° C. The time taken for the composition to cure so that the glasses were firmly stuck together and could no more be moved by hand was measured.

thermal curability and the curability thereof after irradiation with active energy rays is also insufficient.

Example 27, Comparative Example 5

Differential Scanning Calorimetry (DSC)

In Example 27 and Comparative Example 5, the compositions of Example 18 and Comparative Example 4 were compared in the curability before and after irradiation with active energy rays through differential scanning calorimetry (DSC). In DSC measurement, the composition was heated from 20 to

TABLE 4

|  | Example 18 | Example 19 | Example 20 | Example 21 | Example 22 | Example 23 | Example 24 | Example 25 | Example 26 | Comparative Example 4 |
|---|---|---|---|---|---|---|---|---|---|---|
| EXA-850CRP | 100 |  | 100 | 75 | 100 | 100 | 100 | 100 | 100 | 100 |
| EP-4085S |  | 100 |  |  |  |  |  |  |  |  |
| PEMP | 71 |  | 71 | 71 | 71 | 71 | 71 | 71 | 71 | 71 |
| QX30 |  | 88 |  |  |  |  |  |  |  |  |
| Aminimide Compound A | 3.64 | 2.38 |  |  | 3.64 | 3.64 | 3.64 |  |  |  |
| Aminimide Compound B |  |  | 4.07 | 0.81 |  |  |  |  |  |  |
| Aminimide Compound C |  |  |  |  |  |  |  | 4 |  |  |
| Aminimide Compound D |  |  |  |  |  |  |  |  | 4.5 |  |
| Aminimide Compound G |  |  |  |  |  |  |  |  |  | 3.88 |
| Darocure 1173 |  | 0.6 |  |  | 0.95 |  | 0.48 |  |  |  |
| Benzophenone |  |  |  |  |  | 1.06 |  |  |  |  |
| Triethyl Borate |  |  |  |  |  |  | 0.04 | 0.04 | 0.02 |  |
| Benzyl Alcohol |  |  |  |  |  |  |  | 30 |  |  |
| Aerosil R972 |  |  |  |  |  |  | 0.5 |  |  |  |
| Solubility of Aminimide Compound | B | A | B | A | B | B | B | A | A | B |
| 25° C. Storage Stability | 14 days | 28 days | 9 days | 30 days or more | 14 days | 14 days | 21 days | 7 days | 10 days | 30 days or more |
| 25° C. Curability after UV Irradiation (min) | 35 | 420 | 20 | 1200 | 30 | 28 | 40 | 180 | 360 | not cured even after |
| 70° C. Curing Time (min) without UV Irradiation | 70 | 120 | 60 | 190 | 70 | 70 | 75 | 70 | 55 | 24 hours |
| 70° C. Curing Time (min) with UV Irradiation | 5 | 30 | 3 | 80 | 4 | 4 | 5 | 10 | 20 | 100 |

From Examples 18 and 20, it is known that the composition comprising an epoxy resin, a polythiol and the aminimide compound of the present invention can cure at a low temperature of 70° C. even by heating, and that, when irradiated with active energy rays, the curing temperature and the curing time for the composition may be greatly lowered or shortened. From Examples 19, 21, 25 and 26, it is known that, even when the type and the amount of the epoxy resin, the polythiol and the aminimide are changed, there occurs no problem. In addition, it is also known that, when the type and the amount of the aminimide are changed, the curability and the storage stability of the composition can be controlled.

From Examples 22 and 23, it is known that, when the radical generator is further added, then the curability of the composition after irradiation with active energy rays can be enhanced more than that of the aminimide alone.

From Examples 24 to 26, it is known that, when an acid compound is added, then the storage stability of the composition can be greatly improved without any significant influence on the curability thereof. From Example 24, it is known that there occurs no problem even when any other additive such as an inorganic filler is added. From Example 25, it is known that an organic solvent having a high solubility can be added.

From Comparative Example 4, it is known that, when an aminimide compound not to be included in the present invention is used, then the composition is poor in low-temperature 270° C. at a heating rate of 10° C./min in a nitrogen atmosphere, using Seiko Instruments' DSC110.

The composition was irradiated with active energy rays as follows: 50 mg of the composition was taken in a colorless transparent glass-made sample bottle having an inner diameter of 10 mm and a height of 30 mm, and sealed up. At the bottom thereof, the bottle was irradiated with active energy rays in an accumulated quantity of light, 3 J/cm$^2$, using a spot UV irradiator, Hamamatsu Photonics' LC8 (365 nm intensity, 100 mW/cm$^2$). Immediately after irradiated with active energy rays, the composition was analyzed through DSC.

As shown in FIG. 1, it is known that the composition of the present invention started the reaction at a lower temperature and finished the reaction within a shorter period of time than the comparative composition both before and after irradiation with active energy rays.

[Measurement of Adhesion Strength]

The composition of Example 18 was tested for the tensile shear bond strength thereof to iron. Iron test pieces each having a width of 25 mm, a length of 100 mm and a thickness of 1.6 mm were put one upon another so that the overlapping width could be 10 mm, and the composition irradiated with active energy rays under a specified condition was applied between them so that the iron test pieces could be adhered to each other, and cured under a specified condition. After left cooled at room temperature (25° C.) for 2 hours, the sample was tested for the tensile shear bond strength thereof, using a tensile tester (instron) at a pulling speed of 10 mm/min.

The composition was irradiated with active energy rays as follows: 50 mg of the composition of Example 18 was taken in a colorless transparent glass-made sample bottle having an inner diameter of 10 mm and a height of 30 mm, and sealed up. At the bottom thereof, the bottle was irradiated with active energy rays in an accumulated quantity of light, 6 J/cm², using a spot UV irradiator, Hamamatsu Photonics' LC8 (365 nm intensity, 100 mW/cm²).

Example 28

An iron test piece was prepared, using the composition of Example 18. This was left in a temperature-constant furnace set at 80° C. as a specified condition for 40 minutes, then kept cooled in a light shielding room (25° C.) for 2 hours, and thereafter analyzed for the tensile shear bond strength. The tensile shear bond strength was 14.8 MPa.

Example 29

The composition of Example 18 was irradiated with active energy rays at 6 J/cm². Using the composition, an iron test piece was prepared. This was left in a temperature-constant furnace set at 80° C. as a specified condition for 10 minutes and was thereby cured, and then kept cooled in a light shielding room (25° C.) for 2 hours, and thereafter analyzed for the tensile shear bond strength. The tensile shear bond strength was 13.8 MPa.

Example 30

The composition of Example 18 was irradiated with active energy rays at 6 J/cm². Using the composition, an iron test was prepared. This was left in a dark room (25° C.) for 5 hours and was thereby cured, and then analyzed for the tensile shear bond strength. The tensile shear bond strength was 8.0 MPa.

From the results of Examples 28 to 30, it is known that the composition of the present invention rapidly cures and exhibits a strong adhesion force in every case where the composition is cured by heating alone, or is cured by active energy rays combined with heating, or is cured by active energy rays alone, and it is also known that the composition can adhere iron and the like members which do not transmit active energy rays therethrough, by heating alone or by previous irradiation with active energy rays.

While the present invention has been described in detail with reference to specific embodiments thereof, it will be apparent to one skilled in the art that various changes and modifications can be made therein without departing from the spirit and scope thereof.

Incidentally, the present application is based on Japanese Patent Applications No. 2009-144660 filed on Jun. 17, 2009, and the contents are incorporated herein by reference.

Industrial Applicability

The present invention described in the above provides a novel aminimide photobase generator more excellent in low-temperature curability and in photoactivity than existing aromatic aminimide photobase generators, and provides a reaction system and a cured product and also a curing method using the generator. Through irradiation with active energy rays, the composition of the present invention can cure rapidly at a lower temperature, and is usable in various applications for adhesion, sealing, casting, molding, painting, coating, etc.

The invention claimed is:

1. An aminimide compound comprising, in the molecule thereof, a structure represented by the following general formula (I):

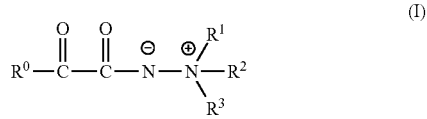

wherein $R^0$ represents a hydrogen atom, an alkyl group which may have a substituent, an aryl group which may have a substituent, or a heterocyclic residue which may have a substituent; $R^1$, $R^2$ and $R^3$ each independently represent a hydrogen atom, or an optional substituent; provided that at least two of $R^1$, $R^2$ and $R^3$ may bond to each other to form a cyclic structure.

2. The aminimide compound according to claim 1, wherein $R^0$ in the general formula (I) is an aryl group which may have a substituent, or a heterocyclic residue which may have a substituent.

3. A composition comprising:
(A) an aminimide compound according to claim 1; and
(B) a compound to be polymerized by a radical and/or a base.

4. The composition according to claim 3, wherein the (B) compound to be polymerized by a base is a compound having at least two epoxy groups in the molecule thereof.

5. The composition according to claim 3, wherein the (B) compound to be polymerized by a base is a mixture of a compound having at least two epoxy groups in the molecule thereof and a compound having at least two thiol groups in the molecule thereof.

6. The composition according to claim 3, wherein the (B) compound to be polymerized by a radical is a compound having at least one ethylenic unsaturated group in the molecule thereof.

7. The composition according to claim 3, which contains the ingredient (A) in an amount of from 0.1 to 50 parts by weight relative to 100 parts by weight of the ingredient (B).

8. The composition according to claim 3, further comprising (C) an active energy ray radical generator.

9. The composition according to claim 8, which contains the ingredient (A) in an amount of from 0.1 to 50 parts by weight relative to 100 parts by weight of the ingredient (B), and contains the ingredient (C) in an amount of from 0.01 to 10 parts by weight relative to 1 part by weight of the ingredient (A).

10. A method for curing the composition according to claim 3, the method comprising subjecting the composition to heating or irradiation with active energy rays, or to both heating and irradiation with active energy rays simultaneously, or to irradiation with active energy rays followed by heating.

* * * * *